United States Patent [19]

Chang et al.

[11] Patent Number: 4,724,270
[45] Date of Patent: Feb. 9, 1988

[54] CATALYTIC CONVERSION OVER DEHYDROXYLATED ZEOLITE

[75] Inventors: Clarence D. Chang, Princeton; Stuart D. Hellring; Richard F. Socha, both of Trenton, all of N.J.

[73] Assignee: Mobil Oil Corporation, New York, N.Y.

[21] Appl. No.: 944,629

[22] Filed: Dec. 19, 1986

Related U.S. Application Data

[63] Continuation-in-part of Ser. No. 783,269, Oct. 4, 1985, abandoned, which is a continuation of Ser. No. 603,049, Apr. 23, 1984, abandoned.

[51] Int. Cl.$^4$ .................................................. C07C 1/00
[52] U.S. Cl. ............................... 585/408; 585/409; 585/415; 585/640
[58] Field of Search ............... 585/408, 409, 415, 640

[56] References Cited

U.S. PATENT DOCUMENTS

| | | |
|---|---|---|
| 3,097,115 7/1963 | Moos | 136/120 |
| 4,016,218 5/1977 | Haag et al. | 260/671 |
| 4,060,568 11/1977 | Rodewald | 260/682 |
| 4,141,859 2/1979 | Plank et al. | 208/139 |
| 4,276,438 6/1981 | Chu | 585/467 |

OTHER PUBLICATIONS

Breck, D. W., Zeolite Molecular Sieves, pp. 493–495.

*Primary Examiner*—Curtis R. Davis
*Attorney, Agent, or Firm*—Alexander J. McKillop; Michael G. Gilman; Malcolm D. Keen

[57] ABSTRACT

The acidity of a zeolite catalyst is reduced by calcination in an essentially water-free atmosphere at temperatures above 700° C., preferably from 725° to 800° C., to reduce the alpha value to less than 10 percent of its original value. The low acidity catalysts produced in this way may be used for conversions requiring low acidity, shape selective catalysis, including conversion of oxygenates to hydrocarbons. The calcined, low acidity catalysts exhibit improved selectivity to certain desired products.

9 Claims, No Drawings

CATALYTIC CONVERSION OVER DEHYDROXYLATED ZEOLITE

CROSS REFERENCE TO RELATED APPLICATIONS

This application is a continuation-in-part of our co-pending patent application Ser. No. 783,269, filed Oct. 4, 1985 which was, in turn, a continuation (FWC) of Ser. No. 603,049, filed Apr. 23, 1984, both now abandoned. The disclosures of those applications are incorporated in the present application.

FIELD OF THE INVENTION

This invention relates to a process for preparing low acidity zeolites and the use of such zeolites in catalytic conversions which are effectively carried out in the presence of low acidity catalysts.

BACKGROUND OF THE INVENTION

Zeolitic materials, both natural and synthetic, are known to have the capability for catalyzing various types of hydrocarbon conversion reactions which take place in the presence of catalytic sites with acidic functionality. These zeolite materials generally have ordered, porous crystalline structures within which there are a number of small cavities that are interconnected by a number of still smaller channels. These cavities and channels are precisely uniform in size within a specific zeolitic material. Since the dimension of these pores are such as to accept for adsorption purposes molecules of certain dimensions, while rejecting those of larger dimension, these materials have commonly been known to be "molecular sieves" and are utilized in a variety of ways to take advantage of the adsorptive propertis of these compositions. The structures may be determined by X-ray diffraction techniques.

These molecular sieves include a wide variety of positive ion-containing crystalline aluminosilicates and other siliceous materials such as borosilicates, ferrosilicates and gallosilicates in which the presence of the trivalent metal at sites within the silicate structure provides the desired acidic functionality in an environment which permits access to the site only by molecules of appropriate size so that the acid catalyzed reactions are carried out in a "shape selective" manner. Metal cations such as sodium which are usually present in these materials when they are synthesized may be converted to the hydrogen form by exchange with ammonium ions followed by heating to drive off ammonia or by direct exchange with an acid such as hydrochloric acid, if the zeolite is not degraded by the acid. Useful catalysts are also produced by a combination of ion-exchange treatments in which the crystalline silicate may be converted to the acid form and then may be ion exchanged with a solution of various metal salts to produce the metal exchanged zeolite.

The acid activity of aluminosilicate zeolites may be so high that conventional hydrocarbon conversion processes and apparatus cannot take full advantage of this high activity. For example, in catalytic cracking, high activity may yield excessive coke formation and the production of large anions of light gases. The acid activity of zeolite catalysts may, however, be lowered to a level at which the use of such catalysts in catalytic conversions is satisfactory and, in fact, results in a considerable increase in the efficiency of such processes. Reactions which have been performed successfully over low acidity zeolites include the conversion of oxygenates such as methanol and dimethyl ether to olefin and other hydrocarbon products, xylene isomerization, aromatic alkylation, and olefin oligomerization, as well as catalytic dewaxing and hydrodewaxing and hydroisomerization. Oxygenate conversion is described, for example, in U.S. Pat. Nos. 3,907,915, 3,894,103, 3,894,104, 3,894,105, 3,894,106, 3,894,107 and 4,560,537. The conversion of oxygenates to hydrocarbons using a fixed bed of catalyst is described in U.S. Pat. Nos. 4,560,536, 4,058,576, 4,044,061 and 3,998,899. The use of a fluidized catalyst bed for this purpose is described in U.S. Pat. Nos. 4,138,440, 4,071,573, 4,406,825 and 3,969,426 to which reference is made for a description of typical examples of these processes.

One method of reducing the activity of aluminosilicate zeolite catalyst is by compositing the zeolite with a matrix material which is relatively inactive. Suitable matrix materials include inorganic oxides, such as those of silica, zirconia, alumina, magnesia and combinations of such materials with one another, as well as clays and other refractory materials.

Other methods to reduce the activity of acid zeolites include cation exchange with sodium or other alkali metal cations or by forming the zeolites with high silica:alumina mole ratios in the structure or framework. An important method in reducing the activity of zeolite catalysts is by a process of steam treating. By controlled steaming, it is possible to produce zeolite catalysts having any desired degree of activity. The degree of steaming of a specified catalyst to achieve a desired activity level is largely dependent upon the nature of the zeolite. Steam treatment, however, often requires long periods of time to treat the catalyst effectively for activity reduction.

U.S. Pat. No. 3,939,058 discloses methods of modifying the catalytic properties of zeolites. One such method is calcination which is defined as heating at high temperatures but below the sintering temperature of the zeolite for varying periods of time. Other methods are also disclosed, including compositing the zeolite in a matrix and steam treatment. The patent further discloses that the crystallinity retention of catalysts may be improved by precalcination of the crystalline aluminosilicate. For example, the patent states that it has been found possible to preserve the crystallinity of aluminosilicates such as the rare earth exchange synthetic faujasites, by calcining the zeolite to drive off water, thus forming a more suitable structure and minimzing loss in crystallinity during subsequent rapid drying, as in spray drying, wet processing, steaming and aging. The calcining may be accomplished by heating the crystalline aluminosilicate sieve after ion exchange to a temperature below the sintering temperature of the sieve and generally in the range of from 500° to 1600° F. (about 260° to 870° C.).

Similarly, U.S. Pat. No. 4,141,859 discloses a method of controlling the relative acid activity of zeolite catalysts, by treating the zeolitic component with air or steam at elevated temperatures, e.g., up to 1700° F. (about 925° C.) in air or at temperatures from about 800° F. to about 1700° F. (about 425° C. to 925° C.).

Calcination of the freshly synthesized zeolite to remove adsorbed water and organic materials that have been used to form the zeolite crystals is necessary to activate the zeolite and accordingly has generally been employed. Also, as stated above, precalcination of the zeolite has been found to stabilize the crystallinity of the zeolite. However, heat treatment may remove hydroxyl groups from the framework of the zeolite. Thus, dehydroxylation of a decationized Y zeolite is discussed in *Zeolite Chemistry and Catalysts*, ACS Monograph 171, pages 142 and 143, in which dehydroxylation of Y zeolite is stated to result from prolonged calcination at relatively high temperatures, resulting finally in the structural collapse of the zeolite and the formation of an amorphous silica or silica-alumina structure. For these reasons, the use of high temperatures has generally been avoided in zeolite synthesis. When organic materials are to be removed from the freshly synthesized zeolite, temperatures of about 1000° F. (about 540° C.) are typical and generally not exceeded in order to avoid damage to the crystal structure.

Calcination or high temperature treatment has been employed in various catalyst treatments to achieve particular results, for example, to convert impregnated metal or other compounds to different forms as described in U.S. Pat. Nos. 4,276,438 and 4,060,568 or to destroy ion exchange capacity as described in U.S. Pat. No. 3,097,115. However, even in such cases the use of higher temperatures, e.g. above 500° C., has not been preferred because of the undesirable effect on the structure of the zeolite.

SUMMARY OF THE INVENTION

In accordance with the present invention, the acid activity (as typically measured by the alpha scale) of intermediate pore size zeolites such as ZSM-5 can be reduced by calcining the zeolites in the absence of water at temperatures greater than about 600° C. but less than the temperature at which the crystallinity of the zeolite collapses. It has been found that the alpha activity of these zeolites can be reduced to less than 10% of the initial alpha value by the high temperature treatment. The resultant low acidity catalysts can be used effectively in catalytic conversions in which low acidity zeolite catalysts are effective to catalyse the conversion reaction. The high temperature treatment to reduce the alpha activity of the present invention takes less time and may yield a more stable catalyst than steam deactivation.

With certain reactions improved selectivity to the desired products may be noted. This is particularly the case with the conversion of oxygenates to hydrocarbons, for example, in the conversion of alcohols and ethers such as methanol or dimethyl ether to hydrocarbons. In these reactions, the selectivity to aromatic hydrocarbons is improved. The conversion is conveniently carried out by passing the oxygenate feed over the thermally treated catalyst at elevated temperature to produce the desired mixture of hydrocarbons. The thermally treated zeolites are particularly suited for the conversion of oxygenates such as methanol to hydrocarbons. In the methanol-to-olefin conversion process, these treated zeolites show a significant increase in both paraffin and aromatic selectivity which is not possessed by zeolites whose acid activity has been reduced by steaming, alkali metal exchange or other means. The improvement has been noted in the fluid bed conversion of oxygenates to hydrocarbons but may also be achieved using fixed bed or moving bed systems.

Other reactions where improved selectivities to desired products are noted include the isomerization of alkylaromatic compounds such as xylenes (where improved selectivity to the para-isomer is noted), olefin oligomerisation, catalytic dewaxing and hydrodewaxing (where improved selectivity of removal of straight and slightly branched chain paraffins may be secured) and paraffin hydroisomerisation.

DETAILED DESCRIPTION

In accordance with the present invention, the alpha activity of a catalyst comprising a crystalline aluminosilicate zeolite having a silica-to-alumina ratio of a least about 12 and a Constraint Index within the approximate range of 1 to 12 can be reduced by heat treating the zeolite at temperatures of 600° C. and above, preferably above 700° C. Non-limiting examples of crystalline aluminosilicate zeolites that can be effectively treated in accordance with this invention include ZSM-5, ZSM-11, ZSM-12, ZSM-23, ZSM-35, ZSM-38 and ZSM-48.

The synthesis and characteristics of zeolite ZSM-5 are described in U.S. Pat. No. 3,702,886; of zeolite ZSM-11 in U.S. Pat. No. 3,709,979; of zeolite ZSM-12 in U.S. Pat. No. 3,832,449; of zeolite ZSM-23 in U.S. Pat. No. 4,076,842; of zeolite ZSM-35 in U.S. Pat. No. 4,016,245; of zeolite ZSM-38 in U.S. Pat. No. 4,406,850 and of zeolite ZSM-48 in U.S. Pat. No. 4,397,827.

These above-defined zeolites can function as catalysts even when modified to have low alpha values, typically less than 10, and even at alpha values substantially lower than 1. As noted above, low acid activity has previously been achieved by using zeolites of very high silica/alumina ratio, extensive ion exchange of the zeolite with sodium or other alkali metal cations, or by severe temperature steaming of zeolites.

In accordance with the present invention, the alpha activity of the above-defined zeolites is reduced by calcining the zeolites at high temperatures, above 600° C., preferably above 700° C., in an essentially water-free atmosphere (although minor, non deleterious amounts of water may be present).

Alpha activity is an approximate indication of the catalytic cracking activity of the catalyst compared to a standard catalyst. Alpha is the relative rate constant (rate of n-hexane conversion per unit volume of oxides, compositions per unit time). It is based on the activity of highly active silica-alumina cracking catalyst taken as alpha=1 (12.5% cracking at 5 minutes on stream). Alpha activity is further defined in U.S. Pat. No. 3,354,078 and the *Journal of Catalysis*, Vol. 4, pages 522-529, August, 1965. The Constraint Index of a zeolite may be determined by the method described in U.S. Pat. No. 4,016,218.

Generally, ZSM-5 and other intermediate pore size zeolites having a Constraint Index of 1-12 are activated by calcining the zeolite at temperatures of about 550° C. to remove water and organic directing agents which are typically included in the synthesis mixture from which the zeolite is made. In accordance with present invention, however, the zeolites are treated above 600° C. and preferably at temperatures from 700° to 800° C. (but less than the sintering temperature of the zeolite) to reduce the acid activity of the zeolite. Although the temperature required for reducing the alpha activity may vary between the individual zeolites the treatment temperature should generally not exceed 1100° C., above which temperature the structural framework begins to collapse.

Calcination is achieved by heating the zeolite at the desired elevated temperature, in dry air, hydrogen or an inert gas such as nitrogen. Typically, the heat treatment proceeds for at least 1 hour, although heating may last between 1-24 hours. The heat treatment is dry (no water), although up to 2% by weight steam may be included in the calcining atmosphere.

It is theorized that at the high temperature used for achieving reduced alpha activity, removal of framework hydroxyl groups is taking place (i.e. dehydroxylation). The heat treatment should not continue beyond the point at which crystallinity of the zeolite is lost. Typically, at least 55% of the crystallinity of the zeolite will be maintained under the heat treatment conditions. However, catalytic activity and selectivity to desired products may be enhanced in spite of the decrease in acid activity, as measured by the alpha value.

The temperature used for the treatment will be at least 600° C. but it has been noted that significant dehydroxylation does not commence at least until 700° C. or higher temperatures. The temperature should therefore be above 700° C., preferably above 725° C. although normally temperatures above 800° C. will not be preferred both for reasons of convenience (special high temperatures equipment will be needed at higher temperatures) and because dehydroxylation has been found to occur most rapidly in the range between 700° and 800° C. Temperatures of 1100° C. will generally not be exceeded.

The final alpha value of the zeolite is typically below 100 and in many cases below 50. Alpha values even lower than this may nonetheless be possessed by catalytically useful materials in reactions requiring only a limited degree of acidity.

-The reactions which may be catalysed by the zeolite treated in this way are those in which a feed is subjected to an acid-catalysed conversion by means of the solid, zeolite catalyst. The acidic sites at which the catalytic reaction mechanisms take place are found within the porous internal structure of the zeolite where access to those sites may be gained by te reactants. The porous structure of the zeolite may also impede egress by the reaction products and therefore it is necessary, if the reaction is to occur, that the reaction products should also be able to leave the pore structure of the zeolite after the catalytic mechanisms have taken place.

The following Examples illustrate the invention. All samples of the thermally deactivated ZSM-5 produced in Examples 1-4 originated from the NH$_4$ form ZSM-5 (SiO$_2$/Al$_2$O$_3$=70), which had been converted into the proton(H)-form by calcination 1° C./min. to 538° C., then held 10 hr., alpha=214.

EXAMPLE 1

An HZSM-5 sample was calcined at 800° C. for 1 hour, then at 1000° C. for 1 hour (alpha=0.4).

EXAMPLE 2

An HZSM-5 sample was calcined at 1000° C. for 1 hour, (alpha=0.9).

EXAMPLE 3

An HZSM-5 sample was calcined at 800° C. for 1 hour, (alpha=12). A mixture of this zeolite (65%) in Al$_2$O$_3$ was used.

EXAMPLE 4

An HZSM-5 sample, as a mixture (65%) in Al$_2$O$_3$, was calcined at 1038° C. for 16 hours (alpha=0.1).

EXAMPLE 5

The conversion of dimethyl ether over the thermally treated zeolite of Examples 1 and 2 is shown in Table 1.

TABLE 1

| Catalyst Example No. | 1 | 2 |
|---|---|---|
| Catalyst Alpha | 0.4 | 0.9 |
| Reaction Conditions | | |
| Pressure (psig) | 0 | 0 |
| Temperature, °F. (°C.) | 900 (480) | 900 (480) |
| LHSV | 1.0 | 1.0 |
| Hours on Stream | 3.3 | 3.0 |
| Major Indicators | | |
| Methanol Conv. (%) | 93.5 | 90.0 |
| Propane/Propene | 0.078 | 0.049 |
| Durene (% of HC) | 0.42 | 0.21 |
| Product Distribution | | |
| H$_2$ | 0.00 | 0.00 |
| CO | 0.00 | 0.00 |
| CO$_2$ | 0.00 | 0.00 |
| H$_2$O | 24.74 | 18.75 |
| MeOH | 6.53 | 10.01 |
| DME | 22.58 | 33.06 |
| Hydrocarbons | 46.14 | 38.18 |
| Hydrocarbon Dist. (wt. %) | | |
| Methane | 4.14 | 5.39 |
| Ethane | 0.18 | 0.27 |
| Ethene | 4.87 | 5.77 |
| Propane | 0.83 | 0.66 |
| Propene | 10.58 | 14.36 |
| Isobutane | 3.32 | 2.42 |
| N—Butane | 0.53 | 0.43 |
| Butenes | 12.77 | 12.20 |
| Isopentane | 4.32 | 1.82 |
| N—Pentane | 0.27 | 0.18 |
| Pentenes | 16.86 | 17.74 |
| C$_6$ Nonaromatics | 23.26 | 23.78 |
| C$_7$+ Nonaromatics | 10.18 | 9.70 |
| Benzene | 0.00 | 0.00 |
| Toluene | 0.15 | 0.14 |
| Ethylbenzene | 0.18 | 0.11 |
| Xylenes | 2.36 | 1.68 |
| C$_9$ Aromatics | 2.38 | 1.58 |
| Durene | 0.42 | 0.21 |
| Other C$_{10}$+ Aromatics | 2.41 | 2.48 |
| Other Indicators | | |
| CH$_2$ Conversion | 62.1 | 44.0 |
| C$_5$+ Percent in HC | 62.8 | 59.4 |
| Aromatics in HC | 7.9 | 6.2 |
| C$_2$-C$_5$ Olefins | 45.1 | 49.2 |

EXAMPLE 6

The conversion of methanol over the thermally treated ZSM-5 catalyst from Example 4 (alpha less than 0.1) is shown in Table 2. The conditions are 2.5 LHSV, 700° F. and 1 atm.

TABLE 2

| Reactor Effluent, wt. pct. | |
|---|---|
| H$_2$ + CO | 0.03 |
| MeOH | 18.14 |
| DME | 58.14 |
| H$_2$O | 23.62 |
| HC | 0.07 |
| HC Composition, wt. pct. | |
| CH$_4$ | 68.0 |
| C$_3$H$_6$ | 11.5 |
| C$_4$H$_{10}$ | 20.5 |
| | 100.00 |

EXAMPLE 7

The conversion of methanol over the thermally treated ZSM-5 catalyst of Example 3 (alpha=12) is shown in Table 3.

TABLE 3

| Reaction Conditions | | |
|---|---|---|
| Pressure (psig) | 0 | 0 |
| Temperature (°F.) | 710 | 830 |
| LHSV | 1.0 | 1.0 |
| Days on Stream | 0.4 | 0.9 |
| Major Indicators | | |
| Methanol Conv. (%) | 84.4 | 100.0 |
| Propane/Propene | 0.16 | 0.11 |
| Durene (% of HC) | 8.79 | 1.25 |
| Product Distribution | | |
| $H_2$ | 0.03 | 0.25 |
| CO | 0.55 | 2.65 |
| $CO_2$ | 0.04 | 0.19 |
| $H_2O$ | 27.65 | 53.74 |
| MeOH | 15.64 | 0.03 |
| DME | 51.51 | 0.07 |
| Hydrocarbons | 4.57 | 43.07 |
| Hydrocarbon Dist. (wt. %) | | |
| Methane | 7.83 | 5.40 |
| Ethane | 0.00 | 0.13 |
| Ethene | 9.26 | 7.09 |
| Propane | 1.98 | 2.17 |
| Isobutane | 5.18 | 8.06 |
| N—Butane | 0.37 | 0.96 |
| Butenes | 3.12 | 15.34 |
| Isopentane | 5.84 | 6.26 |
| N—Pentane | 0.21 | 0.26 |
| Pentenes | 8.79 | 9.54 |
| $C_6$ Nonaromatics | 11.40 | 6.27 |
| $C_7+$ Nonaromatics | 4.90 | 4.13 |
| Benzene | 0.03 | 0.15 |
| Toluene | 0.38 | 1.14 |
| Ethylbenzene | 0.10 | 0.39 |
| Xylenes | 5.05 | 4.90 |
| $C_9$ Aromatics | 9.65 | 5.44 |
| Durene | 8.79 | 1.25 |
| Other $C_{10}+$ Aromatics | 4.88 | 1.82 |
| Other Indicators | | |
| $C_5+$ Percent in HC | 60.0 | 41.6 |
| Aromatics in HC | 28.9 | 15.1 |
| Aromatics in $C_5+$ | 48.1 | 36.3 |
| Durene in $C_5+$ (%) | 14.65 | 3.01 |
| ($C_5+$) + $C_2$-$C_4$ Olefins | 84.6 | 83.3 |

EXAMPLE 8

The conversion of m-xylene over the thermally treated ZSM-5 of Example 2 (alpha=0.9) is shown in Table 4.

TABLE 4

| LHSV | | 6.8 | 1 |
|---|---|---|---|
| Temperature, °F. (°C.) | | 427 (220) | 427 (220) |
| Pressure | | 150 | 150 |
| Time on Stream (Hours) | | 0.5 | 4.5 |
| % Products | Feed | | |
| Toluene | — | 0.08 | 0.95 |
| p | 0.14 | 8.49 | 23.35 |
| m Xylene | 99.86 | 87.59 | 58.81 |
| o | — | 3.51 | 15.46 |
| $C_9+$ Aromatics | — | 0.25 | 1.429 |
| Normalized Xylenes | — | | |
| p | | 8.52 | 23.92 |
| m Xylene | | 87.95 | 60.24 |
| o | | 3.51 | 15.84 |
| p-Xylene | | | |
| % Equilibrium* | — | 36.3 | 101.8 |
| % m-Xylene Converted | — | 12.27 | 41.05 |

*Xylenes equilibrium at 427° C.: 23.5 para, 52.1 meta, 24.4 ortho.

EXAMPLE 9

The oligomerization of propylene over the thermally treated ZSM-5 of Example 1 (alpha=0.4) is shown in Table 5.

TABLE 5

| Reaction Conditions | | | |
|---|---|---|---|
| Pressure (psig) | 0 | 0 | 0 |
| Temperature, °F. (°C.) | 530 (275) | 530 (275) | 750 (400) |
| LHSV | 1.0 | 0.3 | 0.3 |
| Hours on Stream | 2.0 | 3.8 | 8.3 |
| Major Indicators | | | |
| Propene Conversion | 27.40 | 15.33 | 95.61 |
| Propane/Propene | 0.035 | 0.031 | 0.491 |
| Durene (% of HC) | 0.00 | 0.00 | 0.02 |
| Product Distribution | | | |
| $H_2$ | 0.00 | 0.00 | 0.00 |
| CO | 0.00 | 0.00 | 0.00 |
| $CO_2$ | 0.00 | 0.00 | 0.00 |
| Hydrocarbons | 100.00 | 100.00 | 100.00 |
| Hydrocarbon Dist. (wt. %) | | | |
| Methane | 0.00 | 0.00 | 0.05 |
| Ethane | 0.00 | 0.00 | 0.00 |
| Ethene | 0.04 | 0.04 | 1.64 |
| Propane | 2.57 | 2.66 | 2.16 |
| Isobutane | 0.00 | 0.00 | 4.15 |
| N—Butane | 0.00 | 0.00 | 1.78 |
| Butenes | 6.51 | 3.33 | 16.96 |
| Isopentane | 0.00 | 0.00 | 3.80 |
| N—Pentane | 0.00 | 0.00 | 1.06 |
| Pentenes | 6.96 | 3.56 | 19.15 |
| $C_6$ Nonaromatics | 11.31 | 5.74 | 15.61 |
| $C_7+$ Nonaromatics | 0.00 | 0.00 | 25.96 |
| Benzene | 0.00 | 0.00 | 0.00 |
| Toluene | 0.00 | 0.00 | 0.19 |
| Ethylbenzene | 0.00 | 0.00 | 0.08 |
| Xylenes | 0.00 | 0.00 | 0.65 |
| $C_9$ Aromatics | 0.00 | 0.00 | 1.13 |
| Durene | 0.00 | 0.00 | 0.02 |
| Other $C_{10}+$ Aromatics | 0.00 | 0.00 | 1.22 |
| Other Indicators | | | |
| $C_5+$ Percent in HC | 18.3 | 9.3 | 68.9 |
| Aromatics in HC | 0.0 | 0.0 | 3.3 |
| $C_2$-$C_5$ Olefins | 86.1 | 91.6 | 42.1 |

EXAMPLE 10

The effect of high pressure, high temperature aqueous treatment on a thermally deactivated ZSM-5 catalyst (alpha=0.2) is shown in Table 6. Treatment of the catalyst with either methanol or DME (1000 psig) (wherein water is produced over the catalyst) or with water (500 psig) boosts the conversion of methanol or dimethyl ether to near completion. Thus, the reversibility of the thermal treatment is demonstrated. However, when aqueous treatment before conversion was done at 1000 psig, the thermally treated zeolite was completely inactive.

TABLE 6

| Pretreatment Conditions | | | |
|---|---|---|---|
| Feed | — | MeOH | $H_2O$ |
| Pressure (psig) | — | 1000 | 500 |
| Hours on Stream | — | 2.0 | 3.5 |
| Reaction Conditions | | | |
| Pressure (psig) | 0.0 | 0.0 | 0.0 |
| Temperature (°F.) | 900 | 900 | 900 |
| LHSV | 1.0 | 1.0 | 1.0 |
| Hours on Stream | 2.25 | 4.00 | 2.00 |
| Feed | MeOH | MeOH | DME |

TABLE 6-continued

| Pretreatment Conditions | | | |
|---|---|---|---|
| Major Indicators | | | |
| Methanol Conversion | 82.22 | 96.47 | 100.00 |
| Propane/Propene | 0.52 | 0.08 | 0.08 |
| Durene (% of HC) | — | 0.37 | 0.34 |
| Product Distribution | | | |
| $H_2O$ | 23.97 | 53.85 | 37.19 |
| MeOH | 17.78 | 3.53 | — |
| DME | 56.32 | — | 0.04 |
| Hydrocarbons | 1.93 | 42.61 | 62.77 |
| Hydrocarbon Dist. (wt. %) | | | |
| Methane | 38.19 | 2.25 | 2.05 |
| Ethane | 2.54 | — | — |
| Ethene | 11.49 | 9.14 | 8.36 |
| Propane | 7.99 | 2.44 | 2.23 |
| Propene | 15.44 | 30.14 | 27.61 |
| Isobutane | 1.05 | 3.83 | 3.55 |
| N—Butane | 0.43 | 1.21 | 1.12 |
| Butenes | 4.05 | 22.92 | 21.35 |
| Isopentane | — | 2.90 | 2.82 |
| N—Pentane | — | 0.41 | 0.42 |
| Pentenes | 9.68 | 7.45 | 7.05 |
| $C_6$ Nonaromatics | 9.14 | 6.45 | 5.86 |
| $C_7+$ Nonaromatics | — | 4.57 | 7.52 |
| Toluene | — | 0.27 | 0.03 |
| Ethylbenzene | — | 0.17 | 0.03 |
| Xylenes | — | 2.85 | 5.49 |
| $C_9$ Aromatics | — | 2.08 | 3.27 |
| Durene | — | 0.37 | 0.34 |
| Other $C_{10}+$ Aromatics | — | 0.56 | 0.92 |
| Other Indicators | | | |
| $CH_2$ Conversion | 3.90 | 96.50 | 99.90 |
| $C_5+$ Percent in HC | 18.82 | 28.08 | 33.73 |
| Aromatics in HC | — | 6.30 | 10.10 |
| $C_2$-$C_5$ Olefins | 40.70 | 69.60 | 64.40 |

EXAMPLE 11

In this Example, there is demonstrated the activity differene between thermally deactivated ZSM-5 and a high silica ZSM-5. The results of the conversion of DME or methanol to olefis over the respective catalysts are shown in Table 7. Whereas the latter catalyst shows little or no conversion of DME under conversion conditions, the thermally deactivated catalyst yielded roughly 96% conversion of methanol.

TABLE 7

| Reaction Conditions: Ambient Pressure, 900° F., 1 LHSV | | |
|---|---|---|
| Catalyst | | ($Al_2O_3$ extrud.) |
| $SiO_2/Al_2O_3$ | 13,840 | 78 (zeolite = 46) |
| Thermal Treatment | | |
| Temp °C. (Hours) | — | 1000 (1) |
| Alpha | 0.5 | 1.4 |
| | | (orig.-163) |
| Feed | DME | MeOH |
| Hours on Stream | 4.0 | 8.25 |
| Product Distribution | | |
| $H_2$ | — | — |
| CO | 0.68 | — |
| $CO_2$ | — | — |
| $H_2O$ | 0.63 | 54.56 |
| MeOH | 0.95 | 2.49 |
| DME | 94.38 | 1.08 |
| Hydrocarbons | 3.36 | 41.88 |
| Hydrocarbon Dist. (wt. %) | | |
| Methane | 80.04 | 2.23 |
| Ethane | — | 0.10 |
| Ethene | — | 7.20 |
| Propane | — | 1.17 |
| Propene | 6.34 | 33.21 |
| Isobutane | — | 1.69 |
| N—Butane | — | 0.48 |
| Butenes | 13.62 | 19.07 |
| Isopentane | — | 2.64 |
| N—Pentane | — | 0.18 |

TABLE 7-continued

| Reaction Conditions: Ambient Pressure, 900° F., 1 LHSV | | |
|---|---|---|
| Pentenes | — | 8.78 |
| $C_6$ Nonaromatics | — | 8.63 |
| $C_7+$ Nonaromatics | — | 6.37 |
| Toluene | — | 0.08 |
| Ethylbenzene | — | 0.04 |
| Xylenes | — | 3.97 |
| $C_9$ Aromatics | — | 2.32 |
| Durene | — | 0.22 |
| Other $C_{10}+$ Aromatics | — | 1.63 |
| Other Indicators | | |
| $C_5+$ Percent in HC | — | 34.85 |
| Aromatics in HC | — | 8.30 |
| $C_2$-$C_5$ Olefins | 20.00 | 68.30 |
| Propane/Propene | — | 0.04 |
| Durene (% of HC) | — | 0.22 |

One plausible explanation for the increased catalytic activity of any zeolite is greater acid concentration due to enhanced framework aluminum content. Significantly, as shown above, high silica ZSM-5 ($SiO_2/Al_2O_3$ = 13,800) fails to affect methanol conversion despite exhibiting cracking activity substantially the same as that of deactivated samples. This implies that acid concentration in thermolyzed ZSM-5 may already be higher than indicated by alpha values. Since thermolysis does cause zeolite dealumination, access to remaining sites may be blocked by the extra framework aluminum generated. Steaming may simply restore sorptive or diffusion properties to the zeolite by reducing these occlusions.

In effect, zeolite dehydroxylation accentuates the more subtle kinetic character of the three reactions examined. Obviously, activity enhancement due to increased tetracoordinate aluminum (absolute acidity), improved active site access (effective acidity), or some combination thereof, can be discounted.

EXAMPLE 12

Table 8 illustrates xylene isomerization over thermally deactivated ZSM-5.

TABLE 8

| Catalyst ($\alpha$) | | 0.9 | 0.2 |
|---|---|---|---|
| Pressure (psig) | | 150 | 150 |
| Temperature, °F. (°C.) | | 800 (427) | 800 (427) |
| LHSV | | 6.8 | 1 |
| Time on Stream (Hours) | | 3 | 2 |
| Products wt. % | Feed | | |
| Benzene | — | 0.15 | 1.56 |
| Toluene | — | 0.06 | 1.03 |
| Ethylbenzene | 14.79 | 14.02 | 11.38 |
| para | 0.24 | 7.25 | 19.51 |
| meta Xylene | 84.41 | 75.38 | 54.89 |
| ortho | 0.56 | 2.29 | 9.23 |
| $C_9+$ Aromatics | — | 0.85 | 2.40 |
| Normalized Xylenes | | | |
| para | | 8.54 | 23.33 |
| meta Xylene | | 88.77 | 65.63 |
| ortho | | 2.70 | 11.04 |
| para-Xylene | | | |
| % Equilibrium* | | 36.3 | 99.3 |
| % m-Xylene Conv. | | 10.7 | 35.0 |
| % Ethylbenzene Conv. | | 5.3 | 23.1 |

*Xylenes equilibrium at 427° C., p-xylene 23.5, m-xylene 52.1, o-xylene 24.4

EXAMPLE 13

Attempts to conduct toluene disproportionation over a similar catalyst as that in Example 12 (alpha=0.2) yielded only slight conversion. (Table 9).

TABLE 9

| Feed | | | |
|---|---|---|---|
| Temperature (°C.) | — | 482 | 500 |
| Pressure (psig) | — | 0 | 300 |
| LHSV | — | 1 | 1 |
| Time on Stream (Hours) | — | 2.25 | 4.25 |
| WHSV | — | 2.45 | 2.45 |
| Conversion | — | 0.5 | 4.8 |
| Product | | | |
| Benzene | 0.0 | 0.6 | 1.57 |
| Toluene | 99.84 | 99.35 | 95.02 |
| Xylenes | 0.65 | 0.33 | 2.09 |
| Normalized Xylenes | | | |
| para | — | — | 33.6 |
| meta | — | — | 49.1 |
| ortho | — | — | 17.3 |

EXAMPLE 14

Two samples of a catalyst comprising HZSM-5 (40% HZSM-5, 60% silica:alumina binder) were subjected to deactivation by steam and high temperature calcination to final apha values of approximately 50. The steam deactivation was carried out at 750° F.; the high temperature calcination was carried out at 1650° F. (900° C.) in dry nitrogen.

The two deactivated samples were used for the conversion of methanol to hydrocarbons using a fluidized bed microreactor under identical conditions. The results shown in Table 10 below show that selectivity for total aromatics was approximately doubled for the high temperature calcined sample. In addition, the selectivities for isobutane and isopentane were both approximately doubled as compared to the steamed catalyst. The enhanced selectivity for isoparaffin production is of considerable value in the methanol conversion since light gases from a methanol (or DME) conversion unit could be routed to an alkylation unit to enhance the production of high octane gasoline.

TABLE 10

| Comparison of ZSM-5 MTO Catalysts | | |
|---|---|---|
| Catalyst Preparation | | |
| Calcination Temp, °F. (°C.) | 750 (400) | 1650 (900) |
| Atmosphere | STEAM | NITROGEN |
| Alpha of Zeolite | 54 | 40 |
| Reaction Conditions | | |
| Pressure, PSIG | 1 | 1 |
| Temperature, °F. (°C.) | 902 (483) | 900 (482) |
| WHSV | 0.8 | 0.8 |
| Days on Stream | 0.4 | 0.2 |
| Major Indicators | | |
| Methanol Conv, Pct. | 100.01 | 100.0 |
| Propane/Propene | 0.227 | 0.501 |
| Product Distribution, Wt. Pct. | | |
| H2 | 0.03 | 0.02 |
| CO | 0.11 | 0.31 |
| CO2 | 0.03 | 0.21 |
| H2O | 55.77 | 56.04 |
| MEOH | 0.00 | 0.00 |
| DME | 0.00 | 0.00 |
| Hydrocarbons | 44.07 | 43.42 |
| Hydrocarbon Distribution, Wt. Pct. | | |
| Methane | 1.69 | 2.45 |
| Ethane | 0.61 | 0.57 |
| Ethene | 10.48 | 8.63 |
| Propane | 5.36 | 5.94 |
| Propene | 23.60 | 11.84 |
| Isobutane | 8.95 | 16.74 |
| N—Butane | 1.72 | 1.98 |
| Butenes | 14.81 | 6.20 |
| Isopentane | 4.61 | 10.36 |
| N—Pentane | 0.44 | 0.51 |
| Pentenes | 7.68 | 3.32 |
| C6 Nonaromatics | 3.55 | 3.41 |
| C7+ Nonaromatics | 2.00 | 0.78 |
| Benzene | 0.31 | 0.38 |
| Toluene | 1.72 | 2.34 |
| Ethylbenzene | 0.00 | 0.83 |
| Xylenes | 6.10 | 9.29 |
| C9 Aromatics | 4.67 | 10.56 |
| Durene | 0.30 | 1.12 |
| Other C10+ Aromatics | 1.42 | 2.74 |
| Other Indicators, Pct. | | |
| Aromatics in HC | 14.5 | 27.2 |
| C2–C5 Olefins in HC | 56.6 | 30.0 |

We claim:

1. A process for increasing the selectivity of conversion of oxygenates to aromatic hydrocarbons in the catalytic conversion of an organic, oxygenate feed to a hydrocarbon product by contacting the feed with a solid, porous catalyst having a Constraint Index of 1 to 12 and acidic functionality, the catalyst comprising a crystalline aluminosilicate zeolite having a silica:alumina ratio of at least 12, which has been treated to a temperature of at least 725° C. in an essentially water-free atmosphere to reduce its acidity to an alpha value below 100.

2. A process according to claim 1 in which the zeolite is heated to a temperature of 725° to 800° C.

3. A process according to claim 1 in which the zeolite is heated to a temperature of at least 800° C.

4. A process according to claim 1 in which the catalyst alpha is less than 50.

5. A process according to claim 1 in which the catalyst alpha is less than 1.

6. A process according to claim 1 in which the zeolite catalyst is ZSM-5.

7. A process according to claim 1 in which the heat treatment proceeds for at least 1 hour.

8. A process according to claim 1 in which the catalyst retains at least 55% of the crystallinity upon heat treatment.

9. A process according to claim 1 in which the heat treatment proceeds in dry air.

* * * * *